(12) United States Patent
Jia

(10) Patent No.: US 9,657,202 B2
(45) Date of Patent: May 23, 2017

(54) LIVING POLYMER IN SITU SYSTEM AND METHOD OF USE

(71) Applicant: Gaia Dental Products, Inc., Meriden, CT (US)

(72) Inventor: Weitao Jia, Meriden, CT (US)

(73) Assignee: GAIA DENTAL PRODUCTS, INC., Meriden, CT (US)

( * ) Notice: Subject to any disclaimer, the term of this patent is extended or adjusted under 35 U.S.C. 154(b) by 0 days.

(21) Appl. No.: 14/492,647

(22) Filed: Sep. 22, 2014

(65) Prior Publication Data

US 2016/0083631 A1 Mar. 24, 2016

Related U.S. Application Data

(60) Provisional application No. 61/881,077, filed on Sep. 23, 2013.

(51) Int. Cl.
| | | |
|---|---|---|
| *A61K 6/083* | (2006.01) |
| *C08K 3/40* | (2006.01) |
| *C09J 133/10* | (2006.01) |
| *A61K 6/00* | (2006.01) |
| *A61Q 11/00* | (2006.01) |

(52) U.S. Cl.
CPC ............ *C09J 133/10* (2013.01); *A61K 6/0038* (2013.01); *C08K 3/40* (2013.01); *A61Q 11/00* (2013.01)

(58) Field of Classification Search
None
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,479,185 A | 11/1969 | Chambers, Jr. |
| 3,715,331 A | 2/1973 | Molnar |
| 3,751,399 A | 8/1973 | Lee, Jr. et al. |
| 3,926,906 A | 12/1975 | Lee, II et al. |
| 4,058,656 A | 11/1977 | Markiewitz et al. |
| 4,105,519 A | 8/1978 | Pennewiss et al. |
| 4,544,359 A | 10/1985 | Waknine |
| 4,547,531 A | 10/1985 | Waknine |
| 4,659,751 A | 4/1987 | Bowen |
| 5,276,068 A | 1/1994 | Waknine |
| 5,401,783 A | 3/1995 | Bowen |
| 5,444,104 A | 8/1995 | Waknine |
| 5,520,725 A | 5/1996 | Kato et al. |
| 5,684,103 A | 11/1997 | Jia et al. |
| 6,214,101 B1 * | 4/2001 | Nakaseko ............ A61K 6/0017 106/35 |
| 6,730,715 B2 | 5/2004 | Jia |
| 7,090,722 B2 | 8/2006 | Budd et al. |
| 7,906,564 B2 | 3/2011 | Jia et al. |
| 8,222,346 B2 | 7/2012 | Cao et al. |
| 2002/0120033 A1 | 8/2002 | Jia et al. |
| 2012/0142807 A1 | 6/2012 | Jin et al. |

* cited by examiner

*Primary Examiner* — Irina S Zemel
*Assistant Examiner* — Jeffrey Lenihan
(74) *Attorney, Agent, or Firm* — Cantor Colburn LLP

(57) ABSTRACT

A kit for providing a polymerizable resin system is disclosed, which kit comprises a first Part A and a second Part B, which Part A and Part B upon mixing provides a working period of intermediate stage polymerization in which the mixture obtains a desired cohesiveness for a predetermined period of time. The first Part A comprises an acid and the second Part B comprises an organic compound that is water soluble or partially water soluble and that, in the presence of the acid, initiates curing of polymerizable monomer and/or resin that is present in Part A, Part B, or both. Also disclosed is a method of using the mixed composition as an adhesive, cement, glue, sealant, a base liner, a capping agent, a material for surface or structural repair and/or filling, an encasing material, a bodily implant, a dental material, and/or as a polymeric object having a living polymer surface property.

16 Claims, No Drawings derivatives are organic compounds that have been used as free radical initiators in the polymerization of ethylenically unsaturated monomers, especially as photo-polymerization initiators. For example, U.S. Pat. No. 3,479,185 discloses the use of a system comprising N-phenyl glycine or N,N,N',N'-ethylenediamino tetraacetic acid in combination with a 2,4,5-triphenylimidazolyl dimer as a photopolymerization catalyst system.

U.S. Pat. No. 4,058,656 to Markiewitz, et al, discloses a polymerizable system susceptible to free radical polymerization that comprises one or more ethylenically unsaturated compounds and, as an initiator, N-phenyl glycine or a derivative, wherein the initiator will yield a dissolved initiator compound upon acidification, provided that the ethylenically unsaturated compounds do not contain any group with which the acid group of the initiator compound will preferentially react. Markiewitz demonstrated solution polymerization in which polymerization, which occurred over several days in the presence of solvent or water, comprised dissolution and acidification of the initiator in the polymerization system. Markiewitz, however, made no mention of obtaining "living" polymerized materials.

Dental bonding systems utilizing N-phenyl glycine or its derivative compounds as a dentin surface bonding promoter, among other additives, are well known in dentistry. The use of such bonding systems principally follow the techniques outlined in U.S. Pat. Nos. 4,659,751 and 5,401,783, both to R. L. Bowen. To Applicant's knowledge, however, no "living" property has been associated with, or mentioned with respect to, such bonding systems.

On still another subject, organic compounds containing sulfonic acid groups or its alkali salts have been employed as photoinitiators in combination with dissolved chloride ions from a chloride compound, particularly in a process of polymerization using ultraviolet radiation (U.S. Pat. No. 4,105,519 to Pennewisse, et al.). Also, U.S. Pat. No. 5,520,725 to Kato et al. discloses a dental glass ionomer composition comprising (a) an α-β unsaturated carboxylic acid polymer having a weight-average molecular weight lying in a specific range, (b) a polymerizable unsaturated organic compound having a $CH_2=C(R^1)$—COO group, (c) water, (d) an organic aromatic compound having an —$SO_2$ group, (e) a fluoroaluminosilicate glass powder having a mean particle size and specific gravity each lying in a specific range and capable of reacting with the component (a), and (f) a compound containing at least one element selected from the group consisting of aluminum, iron and tin. This composition can be cured either without recourse to conventional redox reaction systems or without exposure to visible light (Abstract and claim 1.) U.S. Pat. No. 6,730,715 to Jia also discloses the use of a sodium salt of bezenesulfinic acid in a dental composition.

LIVING POLYMER IN SITU SYSTEM AND METHOD OF USE

CROSS-REFERENCE TO RELATED APPLICATIONS

Pursuant to 37 C.F.R. 1.78(a)(4), this application claims the benefit of and priority of prior filed co-pending Provisional Application Ser. No. 61/881,077, filed Sep. 23, 2013, which is expressly incorporated herein in its entirety by reference.

FIELD

The present invention relates to a kit in which a two-component resin system capable of use as an adhesive, sealant or filling or encasing material that comprises, in separation components, an organic compound and an acid compound, at least one of which compounds is in association with an inorganic filler and ethylenically unsaturated monomer and/or oligomer.

BACKGROUND

Living polymerization was discovered in the 1950's of last century. It was first demonstrated by Michael Szwarc in 1956 in the anionic polymerization of styrene with an alkali metal/naphthalene system in tetrahydrofuran (THF). Szwarc found that, after addition of monomer to the initiator system, an increase in viscosity would eventually cease but that, the viscosity would start to increase again after addition of a new amount of monomer (en.wikipedia.org/wiki/Living polymerization). Since then, living polymerization has evolved and, in many laboratories around the world, conditions for obtaining such polymerization were discovered for various other types of anionic, cationic, ring-opening and free radical systems. Protection of the living end of a polymer from termination has been accomplished by complexation or by steric hindrance and by appropriate choice of reagents and solvents (Moshe Levy: "Living Polymers"—50 years of evolution).

Recently, U.S. Pat. No. 8,222,346 to Cao et al. disclosed a novel block copolymer, based on living polymerization, containing a controlled distribution of a conjugated diene and a mono alkenyl arene in copolymer blocks. Cao et al. disclosed, in a representative synthetic method, that an initiator compound can be used to start the polymerization of a first monomer. According to this method, the reaction is allowed to proceed until all of the monomer is consumed, resulting in a living homopolymer. To this living homopolymer is then added a second monomer that is chemically different from the first monomer. The living end of the first polymer serves as the site for continued polymerization, thereby incorporating the second monomer as a distinct block into the linear polymer. The block copolymer so grown is living until terminated (col. 1, line 16-26).

Various block copolymers have been prepared by cationic, group transfer, metallocence, and metathesis routes. This includes atom transfer radical polymerization (ATRP), nitroxide-mediated polymerization (NMP), and reversible addition-fragmentation chain transfer polymerization (RAFT). The significant advance in block and graft copolymer synthesis has come about with the advent of controlled radical polymerization (CRP) techniques (*Handbook of Vinyl Polymers, Radical Polymerization, Process, and Technology*; Second Addition, Edited by Mishra, et al, CRC Press; 2009).

BRIEF DESCRIPTION

In one embodiment, the invention is directed to a kit for providing a polymerizable resin system, which kit comprises a first Part A and a second Part B, at least one of which is a paste, which Part A and Part B upon mixing provides a working period of intermediate stage polymerization which provides a manipulative state of cohesiveness for a predetermined period of time (for example, a period of at least 30 seconds), wherein the first Part A comprises an acid and the second Part B comprises an organic compound that is water soluble or partially water soluble and that, in the presence of the acid, initiates curing of polymerizable monomer and/or resin that is present in Part A, Part B, or both.

Another embodiment is directed to a method of forming a cured solid material from polymerizable resin system using a kit comprising mixing a first Part A and a second Part B, at least one of which is a paste, that upon mixing forms a paste that obtains a working period of intermediate stage polymerization that is characterized by a manipulative state of cohesiveness for a predetermined period of time, as measured with a penetrometer, that allows a predetermined working period for applying the mixture; wherein the first Part A comprises an acid and the second Part B comprises an organic compound that is water soluble or partially water soluble and that, in the presence of the acid, initiates curing of the polymerizable monomer and/or resin that is present in Part A, Part B, or both; and employing the mixed composition as an adhesive, cement, glue, sealant, a base liner, a capping agent, a material for surface or structural repair and/or filling, an encasing material, a bodily implant, a dental material, and/or as a polymeric object having a living polymer surface property.

Still another embodiment is directed to a kit for providing a polymerizable resin system, which kit comprises a first Part A and a second Part B, which Part A and Part B upon mixing provides a working period of intermediate stage polymerization in which the mixture obtains cohesiveness, wherein the first Part A comprises polyacrylic acid homopolymer or copolymer and the second Part B comprises an organic compound that is water soluble or partially water soluble and that, in the presence of the acid, initiates curing of a polymerizable monomer and/or resin that is present in Part A, Part B, or both.

With respect to the above embodiments, Part A and Part B upon mixing can obtain a working period of intermediate stage polymerization that is characterized by a cohesiveness corresponding to a stress unit value of at least 0.5 kg/cm$^2$, measured with a penetrometer, which working period lasts for greater than 30 seconds.

DETAILED DESCRIPTION

It has been discovered by the Applicant that a polymerization resin system comprising a "living polymer" in which a working time of at least 30 seconds is obtained, is formable by bulk polymerization, wherein the polymerizable resin system comprises at least an ethylenically unsaturated monomer and/or oligomer and a polymerization initiator system comprising an acid and an effective amount of an organic compound, which is water soluble or partially water soluble and which, in the presence of an acid, can be ionized or solvated to release radical ion groups. Charged groups include, but are not limited to, salts of organic acids (such as sulfonate, phosphonate, carboxylate groups, and salts of amino acids), onium compounds (such as quaternary ammonium, sulfonium, and phosphonium groups), protonated amines, and precursors thereof, as well as combinations thereof.

One aspect of the invention is directed to a kit for providing a polymerizable resin system, which kit comprises a first Part A and a second Part B. Specifically at least one of Part A and Part B, or both is non-liquid or contains polyacrylic acid in liquid or powder form. More specifically, Part A and Part B are both pastes containing a filler. The paste can have various consistency ranging, for example, from a soft and creamy or flowable paste to a doughy or putty like consistency. Components A and B upon mixing (within 6 hours, specifically within 1 hour, more specifically within 30 minutes, and most specifically within 1 to 10 minutes) can provide a working period of intermediate stage living polymerization in which the mixture obtains a polymeric cohesiveness characterized by a stress unit value of at least 0.5 kg/cm$^2$, specifically 0.5 to 2.0 kg/cm$^2$, more specifically 0.8 to 1.9 kg/cm$^2$, for example 0.5 to 1.5 kg/cm$^2$, as measured with a penetrometer, which working period can last for greater than 30 seconds, specifically 45 seconds to 24 hours, more specifically 1 minute to 2 hours. This time period advantageously provides an appropriate working period, depending on where the material is being used, whether for a tiny tooth filling, for which a faster reaction may be desired, for example 30 seconds to a few minutes. In contrast, when filling a larger defect in an architect structure, for example, one would prefer to have much longer time to work with the material, such as 30 minutes to several hours.

As stated above, a first Part A in a kit comprises an acid and a second Part B comprises an effective amount of an organic compound that is water soluble or partially water soluble and that, in the presence of the acid, can be ionized or solvated to initiate curing of the polymerizable monomer and/or resin that is present in Part A, Part B, or both.

In one embodiment, the organic compound comprises a salt of an organic compound that is an organic aromatic sulfonic acid or sulfinic acid and/or an organic aromatic glycine derivative (having the —NH$_2$CH$_2$COO-moiety), specifically a salt of an organic sulfonic acid or organic sulfinic acid, for example, a substituted or unsubstituted phenyl-sulfonic acid and/or phenyl-sulfinic acid. In another embodiment, the organic compound comprises a salt of a compound comprising an aromatic compound having a substitute or unsubstituted glycine moiety. The first Part A, the second Part B, or both, can comprise an inorganic filler in an amount of up to about ninety-five percent by weight of each component, specifically 10 to 80 wt. %, more specifically 20 to 70 wt. % in Part A and/or Part B and or both Part A and Part B.

In one embodiment, the acid in the first Part A comprises poly(acrylic acid) homopolymer or a copolymer (carboxylic acid-group-containing repeat units). The Poly(acrylic acid) can be used in combination with an acid monomer containing a phosphoric acid group or phosphoric acid derivative, for example, a methacrylate monomer having a phosphoric acid group.

Specific ionizable organic compound can include compounds (I) or (II), as follows:

(I) Phenylglycine and derivatives thereof represented by the following structure (1):

$$R^1C_6H_4NR^2CH_2COO^-M^+ \tag{1}$$

wherein $R^1$ is hydrogen or alkyl; $R^2$ is independently hydrogen or alkyl, wherein any alkyl group is substituted or unsubstituted and optionally contains a functional group selected from vinyl, acrylate, or methacrylate; $C_6H_4$ is obviously a phenylene group; $M^+$ stands for a positively charged metal cation to compensate electric charges; and (II) Organosulfur compounds represented by the following structure (2):

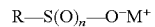

$$R-S(O)_n-O^-M^+$$

wherein n=0, 1, or 2 and R is an organic radical selected from the group consisting of substituted or unsubstituted alkyl or aryl, specifically a radical of benzene or toluene. $M^+$ again stands for a positively charged metal cation necessary to compensate electric charges. Common cations are sodium, lithium, potassium, calcium, and magnesium, and the like.

The polymerization initiation system comprises an acid and an effective amount of an organic compound that is water soluble or partially water soluble and that, in the presence of the acid, can be ionized or solvated to release radical ion groups, and when both the organic compound and acid are present, polymerizes the ethylenically unsaturated monomer and/or oligomer without need of additional external energies of heat, light, or radiation or the like. The acid, one of the components of the living polymerization initiator system, can also be a functional compound that is a monomer/oligomer having an ethylenically unsaturated group and containing an acid group. In this case therefore, a functional monomer/oligomer having an acid group will be polymerized by itself when the ionizable organic compound is present.

The polymerizable resin system can polymerize by bulk polymerization and form a living polymer at room temperature or ambient temperature. When there are two or more different ethylenically unsaturated monomers or oligomers present in the resin system, a networked living polymer or composite can be formed. As can be understood by one of ordinary skill, suspension polymerization is a special situation of bulk polymerization. Methods for suspension polymerization of acrylates and other unsaturated monomers are well known in the art. The process normally comprises dispensing a liquid monomer in an aqueous phase with stirring to form a dispersion of monomer droplets in an aqueous phase.

Without wishing to be bound by theory, it is believed that living polymerization accounts for improved cohesiveness of the polymerization product. The term "living polymer" herein means that, on the basis of what Michael Szwarc has described, a bulk polymerized material is formed from the living polymerization of a polymerizable resin system comprising at least one ethylenically unsaturated monomer and/or oligomer and a polymerization initiator system comprising an acid and an effective amount of an organic compound that is water soluble or partially water soluble and that, in the presence of an acid, can be ionized or solvated to release radical ion groups, wherein upon completion of the polymerization process occurs at least one of the following phenomenon: (1) the increase in viscosity in forming a solid is eventually stopped if there is oxygen present to cause inhibition, but that curing/hardening resumes when the oxygen is consumed and/or the supply of oxygen is blocked; or (2) the polymerized mass firms up or becomes jelly-like, which mass can take the shape of the container in which polymerization has occurred; or (3) in the absence of oxygen, the polymerized polymer becomes a hard solid and its surface and/or internal structure becomes, therefore, "dry," which solid is touchable without seeming wet on the touching surface wherein, like other dormant situations, the solid polymer is still capable of causing subsequent layer or layers of a polymerizable resin composition (comprising at least one ethylenically unsaturated resin that is inactive by itself in normal storage conditions) to further polymerize when added to the "living polymer" surface. Thus, a di-, tri- or multiple layered block polymer structure can be obtained.

Since bulk polymerization is employed, the above-described "living polymerization" process and the "living polymer" product generated from the polymerization can be used, either in situ or not, in many fields or situations, for example, as a glue, an adhesive, a sealant, a surface or a structural defect filling or repairing material, a structural component, a medical device such as bone cement, an implant, or a dental material (such as a bonding agent, a cement, restorative composite, root canal sealant, base liner, pulp capping agent, or the like), a dental appliance, an encasing material, or simply a polymeric article that possesses surface characteristics due to the living polymer properties. One of the advantages of the cured polymeric structure having living properties is that, without limitation, the surface can be further repaired and/or modified with an "inactive" resin component, which component otherwise has practically unlimited shelf-life or requires mixing with another component or requires external energy in order to use it.

For example, the inside of an article made from the living polymer can be conductive, while an outside layer can be non-conductive, which article can be produced from sequential addition of a resin composition co-polymerized onto the surface of the living polymer. To make the polymer conductive, micro- or nano sized particulates and/or fillers of silver, graphene, or the like can be incorporated into the formulation of the resin composition.

There are also situations where a pre-made polymeric object (article) having "living" characterizations as described herein can be processed using the polymerizable resin system and then delivered to a site where the article can be placed or filled. The pre-made article can "glued" into place using an ethylenically unsaturated polymerizable adhesive composition that is polymerizable merely by contacting the living polymer surface, so that the adhesive composition is allowed to cure to secure the pre-made "living" article at the desired site. For example, a dentist, in order to restore a patient's damaged tooth, can subscribe a restoration such as a dental crown or bridge from a dental lab, which restoration is made from the living polymerizable resin system. The dentist can simply place and adhere the restoration onto the patient tooth with a polymerizable resin which by itself has no ability to cure whatsoever. Similarly, a dentist can make an inlay directly from a patient's damaged tooth using the living polymerizable resin system and then lift it, subsequently apply a polymerizable resin layer that contains an acid onto the tooth surface, and seat the inlay to allow curing. The benefit of such a practice is that complete seating of the restoration is allowed, minimizing the potential gap between the restoration and tooth surface, etc. Furthermore, it can eliminate potential exothermic reaction commonly associated with dental resin cements through redox chemical reaction such as employ a benzoyl peroxide/amine curing system.

As a practical manner, when an application requires that living polymerization taking place in situ, the polymerization resin system can be divided into at least two components, or two parts, for the purpose of storage and preserving the polymerizable resin system. Therefore, a kit for a polymerization resin system having at least two parts or components can be formulated. For example, the organic compound, which is water soluble or partially water soluble and that, in the presence of an acid, can be ionized or solvated to release radical ions, can be in one stand-alone part, which can be labeled as Part A; while the acid can be contained in association with the ethylenically unsaturated monomer/oligomer as a second part and can be labeled Part B. In use, Part A and Part B can be simply mixed in a predetermined ratio and the mixed resin system transferred into the place where needed, letting the resin system polymerize thereafter. As an alternative, the organic compound (which is water soluble or partially water soluble and which, in the presence of acid, can be ionized or solvated to radical release ions) can be premixed into an inert medium carrier, a non-reactive ethylenically unsaturated resin monomer mix, a solvent, and so on, as Part A of the polymerizable resin system. It can also simply be pre-deposited or coated onto a mixing brush, a mixing spatula, a mixing surface, or the like, used to mix the Part B polymerizable resin system. In addition, the organic compound can be subject to surface coating, thereafter forming encapsulated particulates/solids that are not reactive when they are mixed within the polymerizable resin system. Thus, a storage stable "all-in-one" polymerizable resin system can therefore be formed, in which the two Parts are in the same container. When effective mixing and/or smear action is applied to the encapsulated initiator particulates to cause their breakage for releasing the active organic compound, living polymerization can occur to form the living polymer from the composite.

Since acid or acid-group containing resin component(s) can be formulated into a composition as a polymerization catalyst, the adhesion-promoting effect to underlining structure surfaces, on which the composition is applied, is apparent. Under certain situations it can be desirable, although not required, to neutralize or consume the acid when it has achieved its catalytic effect for polymerization. This can be accomplished in several ways, for example, by using acid reactive filler (which is essentially a base) or an epoxy resin in the composition (see the disclosures of U.S. Patent Published Application No. 2012/0142807 to Jin et al.).

In one embodiment of a kit, a two-part self-curable composition contains at least one ethylenically unsaturated resin monomer or oligomer, in which the acid is kept in one part (which may be named Catalyst) and the organic compound (which is water soluble or partially water soluble and which, in the presence of an acid, can be ionized or solvated to release radical ion groups) is formulated into the other part of the curable system (which may be named Base). The ethylenically unsaturated polymerizable resin can be formulated either in the Catalyst part or the Base part or both, as long as it will not interfere with the storage stability of each part when incorporating the living polymerization initiating components within.

Since the organic compound is water soluble or partially water soluble and that, in the presence of an acid, can be ionized or solvated to release radical ion groups, water participating in the polymerization reaction is inevitable. Therefore, it is desirable to purposely add some water to the system, either in the Base part and/or the Catalyst part. However, the water content participating in the living polymerization process can also come from the acid compound itself, from the moisture content of the ingredients used, and/or simply from the environment where the living polymerization is occurring. In that case, the intentional addition of water into the system formula may be unnecessary.

One of the unexpected advantages of using a self-curable composition possessing living properties is that, because of its living nature during the polymerization process, curing of the composition after mixing the two parts together starts the polymerization and makes the mass firm up or viscosity increase. Thereafter, however, another time period of at least 30 seconds is provided, which time period sometimes can be up to a day or more, that allows workability during the course of the polymerization/curing, specifically allowing the user manipulation, such as material transferring, packing, shaping, condensing or like actions to the bulk mass of the curing material formed in situ. The material, although it is already in the process of the polymerization, can be subjected to cutting into, flipping over, or folding and pressing together during that working period without the messy situation commonly seen for such action with a soft liquideous material. This uniquely extended workability time period can be referred to as an "intermediate stage of living polymerization" or "intermediate state of polymerization" and it is more prominent with a formula into which particulate filler or fillers have been incorporated. This feature can be very beneficial for many applications. For example, the packing or condensing action can eliminate voids within a filling material and remove any gap between the filling material and underneath structure surfaces, etc.

There are many ethylenically unsaturated resin monomers/oligomers that can be suitably used in the living polymerization reaction and form a living polymer or a living polymer composite thereafter. The polymerizable monomer/oligomer is not particularly limited as long as it comprises a monomeric unit that can be polymerized through the living polymerization described herein, for example having a (meth)acryloyl group, styryl group, vinyl group or allyl group as a polymerizable group. Typically, resin compounds having a vinyl group are of ethylenically unsaturated nature and contain an olefinic double bond. Examples of those monomers are acrylonitrile, acrylamide, (meth)acrylates, aldehydes, butadiene-1,3, ethylene, isoprene, methacrylic esters, methacrylamide, methyl styrene, styrene, vinyl esters, vinylidene chloride, N-vinyl pyrrolidone, and so on. Specific resin monomers include those based on acrylic and methacrylic molecules, for example, those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"), urethane acrylates or diacrylates, urethane dimethacrylates (hereinafter abbreviated "UDMA"), triethylene glycol dimethacrylate (hereinafter abbreviated "TEGDMA"), polyethylene glycol dimethacrylate (hereinafter abbreviated "PEGDMA"), hexanedioldimethacrylate (hereinafter abbreviated "HDDMA") and polycarbonate dimethacrylate (hereinafter abbreviated "PCDMA"), which are commonly-used principal oligomers/polymers suitable for use in the present invention. Resins also include a biodegradable methacrylate such as polylactide methacrylate (PLAMA) which is a polymerization product of lactide with 2-hydroxyethyl methacrylate (HEMA) as disclosed in commonly assigned U.S. patent application No. 20020120033, which is hereby incorporated by reference. Other polymerizable (meth)acrylate monomer include aliphatic esters of (meth)acrylic acid such as methyl (meth)acrylate, ethyl(meth)acrylate, propyl(meth)acrylate, isopropyl(meth)acrylate, butyl(meth)acrylate, pentyl(meth) acrylate, isopentyl(meth)acrylate and hexyl(meth)acrylate; aromatic esters such as phenyl(meth)acrylate; glycidyl (meth)acrylate and tetrahydrofurfuryl(meth)acrylate; (meth) acrylates containing a hydroxyl group and further an aromatic ring such as 2-hydroxyethyl(meth)acrylate, 2- or 3-hydroxypropyl(meth)acrylate, and so on; glycerol mono (meth)acrylate, diethylene glycol mono(meth)acrylate, polyethylene glycol mono(meth)acrylate, and polyethylene glycol mono(meth)acrylates having a methyl or ethyl substituent such as ethylene glycol mono(meth)acrylate, diethylene glycol mono(meth)acrylate, polyethylene glycol mono (meth)acrylate, methoxydiethylene glycol mono(meth) acrylate, methoxytetraethylene glycol(meth)acrylate; aliphatic esters of (meth)acrylic acid such as methylene glycol di(meth)acrylate, neopentyl glycol di(meth)acrylate and 1,3-butylene glycol di(meth)acrylate; polyethylene glycol di(meth)acrylates such as ethylene glycol di(meth)acrylate, diethylene glycol di(meth)acrylate, pentaethylene glycol di(meth)acrylate, nonaethylene glycol di(meth)acrylate and tetradecaethylene glycol di(meth)acrylate, etc. Polyfunctional polymerizable monomers/oligomers with tri- or more polymerizable groups such as trimethylolalkane tri (meth)acrylates including trimethylolmethane tri(meth)acrylate, trimethylolethane tri(meth)acrylate and trimethylolpropane tri(meth)acrylate, tetra(meth)acrylates of polymethylolalkanes or ethers thereof including pentaerythritol tetra(meth)acrylate and ditrimethylolpropane tetra(meth)acrylate, and so on, may also be utilized.

The above polymerizable monomers/oligomers can be used alone or in combination of two or more. If the polymerizable monomer/oligomer contains an acid group in its molecule, however, this acid(s) containing polymerizable monomer/oligomer may be used on its own or in combination with another in the polymerizable resin system to form the living polymer/composite.

Epoxy containing resins can also be incorporated into the polymerizable methacrylate system and utilized in the living polymerization and copolymerized. Reference is hereby given to the U.S. Published Patent Application No. 2012/0142807 to Jin et al., hereby incorporated by reference. All the epoxy compounds and methacrylate monomers disclosed therein are suitable for use in the present living polymerization system. Since the acid can also be used to polymerize an epoxy compound, it can be feasible and desirable to combine the living polymerization with the epoxide ring opening.

Technically, any organic or inorganic acid can be satisfactorily used as part of the living polymerization initiation system. Chemical compounds containing acid groups of carboxylic acid (—COOH), phosphorus-containing acid groups (—PO(OH)$_3$, —OPO(OH)$_2$, —PO(OH)OR, —OPO(OH)OR, etc.), sulfur-containing acid groups (—SO$_2$H, —SO$_3$H, —OSO$_3$H, etc.), boron-containing acid groups (—B(OH)$_2$, —OB(OH)$_2$, —B(OH)OR, —OB(OH)OR, etc.) are all suitable acids.

It has been found that to obtain the best or improved polymer properties, acids in polymeric or macromolecular form can be employed, for example, poly(acrylic acids) and resin oligomers containing acid group(s), because the acids become part of the living polymer structure, either through co-polymerization or hybridization, when the polymerization reaction completed. Specific acid-containing molecules include aliphatic or aromatic polymerizable resin monomers or oligomers. Poly(acrylic acids) can be in liquid or solid, specifically powder form and can have a weight average molecular weight ranging from 1000 to 1,000,000, specifically 50,000 to 500,000. Poly(acrylic acids) are commercially available from a variety of sources including Evonik under the trademark Degacryl.®

These polymerizable monomers or oligomers can comprise at least one acid or acid-precursor functional group, such as a carboxylic acid, carboxylic acid anhydride, acyl halide, sulfonic acid, sulfonyl halide, sulfonic anhydride, sulfinic acid, sulfinyl halide, sulfinic anhydride, phosphoric acid, phosphoric acid derivative, phosphonic acid, and phosphonic acid derivative, and combinations thereof. Additionally, the polymerizable monomers or oligomers can comprise at least one polymerizable unsaturated carbon-carbon bond, such as an alkene or alkyne functional group.

Suitable organic compounds that are water soluble or partially water soluble and that, in the presence of an acid, can be ionized to release radical ions, include phenylglycine and derivative or analogue compounds having the following representative structure:

$$R^1C_6H_4NR^2CH_2COO^-M^+ \quad (1)$$

wherein $R^1$ is hydrogen or an alkyl group; $R^2$ is hydrogen or an alkyl group, which alkyl group can contain a substituent or a functional group selected from vinyl, acrylate, or methacrylate. The $M^+$ stands for a cation such as mono-positively charged metal cation or the equivalent of a multi-positively charged metal cation necessary to compensate electric charges. Common cations are those of sodium, lithium, potassium, calcium, and magnesium, and the like. Specific compounds are the salts (for example, of alkali or alkaline earth metals) of the addition reaction product of N(p-tolyl)glycine and glycidyl methacrylate (NTG-GMA); and the adduct of N-phenylglycine and glycidyl methacrylate (NPG-GMA). More specifically, the organic compound is the sodium or magnesium salt of NTG-GMA and/or an organosulfur compound represented by the following structure:

$$R\!-\!S(O)_n\!-\!O^-M^+ \quad (2)$$

wherein n=0, 1, or 2; R denotes an organic radical such as a substituted or unsubstituted alkyl or aryl group; $M^+$ independently can be as defined above, specifically $M^+$ stands for a cation such as a mono-positively charged metal cation or the equivalent of a multi-positively charged metal cation necessary to compensate for electric charges. Cations of sodium, lithium, potassium, calcium, and magnesium, or the like are common. Specific organosulfur compounds are alkali salts of phenyl-sulfonic and sulfinic acids. If $M^+$ and R occur more than once in organic compounds used in a composition, they can denote different cations or groups, respectively.

In the above structure (2), suitable alkyls are straight-chain or branched $C_1$-$C_{10}$ alkyl groups which can optionally be substituted. Specifically, the alkyl group is a $C_1$-$C_4$ alkyl such as methyl, ethyl, n-propyl, isopropyl, n-butyl, sec-butyl, isobutyl or tert-butyl, more specifically a methyl group. Substituents other than hydrogen can be used in these radicals, for example halogens such as fluorine, chlorine, bromine or iodine, oxygen-containing substituents such as oxy, alkoxy and/or hydroxy radicals, and/or nitrogen-containing substituents such as amino and/or imino radicals. Specifically, hydroxy or amino and imino radicals can be used, more specifically, a 1-hydroxyalkyl radical, in particular a 1-hydroxyethyl or 1-hydroxymethyl radical (R=CH$_3$—CH(OH)— or HO—CH$_2$—) or an amino/imino methyl radical (R=H$_2$N—(HN)C—) or condensation products of the hydroxyalkyl radicals with ammonia (R=H$_2$N—CHR'—, $M^+$O—(O)S—CHR'—NH—CHR'— or [$M^+$—O—(O)S—CHR']$_2$N—CHR'—), wherein R' can be, for example, a substituted or unsubstituted $C_1$-$C_6$ alkyl or $C_6$-$C_9$ aryl group.

In the above structure (2), suitable aryls are aromatic radicals containing at least six carbon atoms, which are optionally substituted, specifically substituted or unsubstituted phenyl groups such as a benzene or toluene group. Substituents other than hydrogen can be used in these radicals, for example halogens such as fluorine, chlorine, bromine or iodine, oxygen-containing substituents such as alkoxy and/or hydroxy radicals and/or nitrogen-containing substituents such as (alkyl)amino radicals.

At least 0.2% by weight of the organic compound (1) and/or (2) can be present in one part of a kit or system, using one or combined organic compounds that are water soluble or partially water soluble and that, in the presence of an acid, can be ionized to release radical ions as the initiator component in order to have a meaningful living polymerization effect and a reasonable polymerization time and living polymer properties.

The compositions, specifically Part A and/or Part B, can further comprise at least one filler known in the art, for example a filler used in dental restorative materials. Generally, the filler can be added in an amount of up to about ninety-five percent by weight of each Part in a two-component or two-part system. Suitable fillers are those capable of being covalently bonded to the polymeric matrix that is formed from the resin itself or to a coupling agent that is covalently bonded to both. Examples of suitable filling materials include but are not limited to those known in the art such as mineral clay particulates, silica, silicate glass, quartz, barium silicate, barium sulfate, barium methacrylate, zirconium methacrylate, strontium silicate, barium borosilicate, strontium borosilicate, borosilicate, lithium silicate, amorphous silica, calcium phosphates such as calcium hydroxyapatite and amorphous calcium phosphate, calcium oxide, calcium hydroxide, alumina, zirconia, tin oxide, tantalum oxide, zinc oxide and titania. Particularly suitable fillers for dental filling-type materials, for example, prepared in accordance with this invention are those having a particle size ranging from about 0.1-10.0 microns with a silicate colloid of 0.001 to about 0.10 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and 4,547,531 to Waknine, the pertinent portions of which are incorporated herein by reference. Suitable organic filler materials are known in the art, including for example the poly(methacrylate) fillers described in U.S. Pat. No. 3,715,331 to Molnar. A mixture of organic and inorganic filler materials can also be used.

Fillers capable of being bonded to molecules containing an acid group through ionic bonding can also be used in the compositions. Examples of such fillers are well known in dentistry, which are acid-reactive fillers based on the fluoroaluminosilicate (FAS) glass fillers. They are also called glass ionomer cement fillers (GI filler). In addition to the FAS glass fillers, other acid-reactive fillers can also be used, including metallic oxides and hydroxides, such as zinc oxide, calcium oxide and calcium hydroxide. Acid-reactive fillers, as disclosed in U.S. Pat. No. 7,090,722, are also suitable. If the composition is intended for dental or medical uses, fillers having mineralization or therapeutic effects may also be incorporated in the composition. Examples of those fillers are well known in the art, such as bioactive materials including any substance or metabolic precursor thereof, which is capable of promoting growth and survival of cells, tissues, and bone. Suitable bone growth promoting substances include but are not limited to bioglass, Portland cement, hydroxyapatite, tricalcium phosphate, a substance having a phosphate to calcium ratio similar to natural bone, calcium hydroxide, or other suitable calcium-containing compounds, and the like. Some of these afore-mentioned calcium-containing fillers by themselves may be a base in nature, which are reactive to the acid. A bone growth promoting substance can be in the form of a particulate or fiber filler in nano, micro or macro form, or mixtures thereof, bone chips, bone crystals or mineral fractions of bone and/or teeth, a synthetic hydroxyapatite, or other suitable form.

In one embodiment, a paste-paste two-part system comprise a first part in which the acid reactive filler(s) is kept in the part where the organic compound is present (which organic compound is water soluble or partially water soluble, and, in the presence of an acid, can be ionized or solvated to release radical ion and non-acid or acid-group containing resin part (Base) and a second part in which the acid non-reactive filler(s) is contained in the acid or acid-group containing resin part (Catalyst). Of course, additional non-reactive fillers can also be incorporated into any part of the paste-paste self-curable two-part compositions in order to modify the properties, such as viscosity and handling.

Additional components can also be added to the two-part systems, to each part, or to one part only. Additives can include, but are not limited to, second polymerization initiators such as photoinitiators and/or redox initiators, polymerization inhibitors, stabilizers, UV absorbers, radiopaque materials, fluorescent agents and therapeutic agents. The second redox initiator can be chosen from a conventional system such as, but not limited to, a benzoyl peroxide/amine system, hydroperoxide/thiourea system and (thio)barbitoric acid compound/copper or iron halide system. The amount of addition, however, should be formulated so not to be a primary factor in the initiation reaction, rather having a synergetic effect to accelerate the reaction. Specifically, peroxide initiators and/or photoinitiators can be essentially absent from the two-part system.

Examples of inhibitors can include, but are not limited to, butylated hydroxytoluene, hydroquinone, benzoquinone, phenol, and the like. A preferred polymerization inhibitor is 2,6-di-tert-butyl-4-methylephenol (BHT). The inhibitor can be used to scavenge small amounts of free radicals during storage and to improve the shelf stability of the polymerizable system. More than one inhibitor can be used in the system of the invention. For example, in a two-paste system, both the catalyst paste and the base paste can contain a polymerization inhibitor. The polymerization inhibitor can be specifically present in an amount up to about 2% by weight, more specifically from about 0.001% to about 1% by weight.

While not intending to be bound with theory, the speculation for the mechanism of the discovered bulk living polymerization process follows an anionic vinyl polymerization reaction. The acid presence in the reaction system may serve as a catalyst, which may offer a polar system and give an environment of ionization or solvation of the organic compound initiator which is water soluble or partially water soluble. In the presence of an acid, the organic compound initiator may be ionized or solvated and therefore able to offer radical ion groups and get activated. Contrarily to the common knowledge that radicals or radical ions are short lived species during a polymerization process, the radical ions in the present living polymerization system are somehow longer lived. According to the ionic polymerization theory by M. P. Stevens (Section 7.3 Anionic Polymerization, Chapter 7, Polymer Chemistry—An Introduction; Third Addition, 1999 by Oxford University Press, Inc.), the mechanism of anionic polymerization may involve simple addition of anion to the vinyl group (it is the (meth)acrylate group(s) in this case); or the initiation may be brought about by charge transfer by the free alkali metals or by addition complexes of alkali metals and unsaturated or aromatic compounds. According to Stevens, living anionic polymers can be made when the polymerization temperature is kept low (about −78° C. in most instances) and the reactions are usually conducted in a solvent system. A redox reaction and/or free radical induced polymerization of the current inventive system, on the other hand, is also possible.

The termination of the living polymerization of the inventive polymerizable composition can be achieved through applying an external energy such as visible light radiation, heating, etc. during or after the polymerization or surface interruption, contamination, and/or mechanical polishing after the polymerization.

The kit or method of the present invention can have wide utility. In one embodiment, the kit and polymerizable resin system is used to provide solid supportive matter for a biological substance. The biological substance can be a bone and tooth structure. Specifically, the polymerizable resin system is a dental composition for use as a cement or restorative filling material, a bonding agent, a restorative composite, a root canal sealant, base liner, or a pulp capping agent.

In another embodiment, the kit and polymerizable resin system is used to provide solid supportive matter for a non-biological substance. The non-biological substance can be selected from the group consisting of wood, polymer, glass, ceramic, metal or metal alloy, stone, concrete, and composite materials comprising at least two of the foregoing substances.

The method can comprise using the polymerizable resin system to fill a space by packing and condensing actions during the working period of intermediate stage polymerization. The polymerizable resin system can be advantageously used in situ. For example, the mixture of Part A and Part B can be injected into a tooth cavity as a restorative material that is allowed to firm up to reach the working period (the intermediate stage of living polymerization), wherein a dentist is able to use a dental instrument to pack, shape, adapt or condense the restorative material into the cavity for at least 30 seconds before it reaches the set state.

In another embodiment, the polymerizable resin system can be used to form a pre-made polymeric article (object) having a living-polymer surface that is delivered to another location for use in filling a space or for placement in a predetermined site. The pre-made polymeric object can be glued into the predetermined site using an ethylenically unsaturated polymerizable adhesive composition that is polymerizable by contact with a polymer surface of the polymeric article in order to secure the pre-made polymeric article in the predetermined site. For example, the pre-made polymeric article can be a dental crown or bridge, an inlay/onlay, or a root canal point or post. Root canal points and posts are usually pre-made by a dental device manufacturer and subsequently used to restore a damaged tooth.

Following are illustrative examples of the living polymerization and compositions comprising living polymers formed therefrom.

EXAMPLES

Abbreviations of the materials used in the examples and their descriptions are provided in Table 1.

TABLE 1

| Abbreviations | Material's full name and description |
|---|---|
| EGMPA | Ethylene Glycol Phosphate Methacrylate or HEMA Phosphate |
| CD9038 | Highly Ethoxylated Bisphenol A Diacrylate Esters from Sartomer Co. |
| CN972 | An aromatic urethane acrylate from Sartomer Co. |
| UDMA | Urethane Dimethacrylate |
| GDMA | Glycol Dimethacrylate |
| TEGDMA | Triethyleneglycol Dimethacrylate |
| BisGMA | Bisphenol A Glycidyl Methacrylate |
| HDDMA | 1,6-Hexanediol Dimethacrylate |
| HEMA | Hydroxyethyl Methacrylate |
| 4-META | 4-methacryloxyethyl trimellitic anhydride or 4-methacryloxyethyl trimellitic acid |
| Epoxy 06 | A cycloaliphatic epoxide resin, available from Synasia, NJ |
| PAA powder | Polyacrylic acid, $M_w$ = 450,000 (powder), available from Sigma-Aldrich |
| PAA liquid | An aqueous solution of polyacrylic acid copolymer containing about 40% solid, Degacryl ® 4997L, available from Evonik Industries, Germany. |
| GI filler | An average of about 4 micron particle sized acid reactive glass ionomer filler, SP2034, ® available from Specialty Glass, Inc., Fl. |
| Barium Glass filler | A silane surface treated barium-boron-silicate dental glass filler with particle size of about 2.0 microns, V-119-4120, ® available from Esstech Inc., Pa. |
| PMMA | Poly(methyl methacrylate) powder |
| Na•BSA | Sodium salt, benzenesulfinic acid, 98% purity |
| Li•p-TSA | Lithium salt, p-toluenesulfinic acid, 98% purity |
| Na•p-TSA | Sodium salt, p-toluenesulfinic acid, 98% purity |
| NTG-GMA•Na | Surface Active Monomers, NTG-GMA, Sodium Salt, from Esstech Inc. |
| NTG-GMA•Mg | Surface Active Monomers, NTG-GMA, Magnesium Salt, from Esstech Inc. |
| BPO | Benzoyl Peroxide |
| DHEPT | N-N-bis(2-hydroxyethyl)-P-toluidine |
| EDMAB | Ethyl-4-dimethylamino benzoate |
| CQ | Camphorquinone |
| BHT | 3,5-Di-tert-butyl-4-hydroxytoluene |

To illustrate polymerization/curing using the two-part self-curable compositions, wherein living polymer and/or composite formation was obtained through a polymerization process using a polymerization initiation system comprising an organic compound (that is water soluble or partially water soluble and that, in the presence of an acid, can be ionized or solvated to release radical ion groups) and an acid or acid-containing compound for the polymerization of an ethylenically unsaturated monomer and/or oligomer, a resin composition is first premixed per the formula as indicated in Table 2 in the following Examples 1 to 11. Then the organic compound is either used as is or premixed into a solution or dispersion or the like and mixed with the another part of the resin composition in the ratio as indicated using a dental spatula or mixing tip in a dental mixing well right before observation of the living polymer formation.

TABLE 2

| Example No. | Catalyst Part (Parts per hundred by weight) | Base Part (Parts per hundred by wt. when compounded into a formula) | Hardening Time |
|---|---|---|---|
| Example 1 | 4-META (10.3) UDMA (13.7) HEMA (5.1) TEGDMA (5.1) CQ (0.1) EDMAB (0.2) BHT (0.01) Silane treated Barium Glass filler (65.4) | BisGMA (10.6) UDMA (10.6) HDDMA (10.8) Silane treated Barium glass filler (65) NTG-GMA•Na (3) | 10 minutes |
| Example 2 | PAA liquid | HEMA (90) NTG-GMA•Na (10) | 10 minutes |
| Example 3 | PAA liquid | HEMA (19) NTG-GMA•Na (2) CN972 (12) GI Filler (67) | 15 minutes |
| Example 4 | PAA ($M_w$ = 450,000) (powder form) | The same part from Example 2 | 20 minutes |
| Example 5 | The same part from Example 1 | The same part from Example 2 | 10 minutes |
| Example 6 | The same part from Example 1 | NTG-GMA•Na | NA |
| Example 7 | PAA liquid (27.0) HEMA (7.0) Silane surface treated barium glass filler (66.0) | GDMA (13.6) UDMA (11.56) TEGDMA (2.04) Li•p-TSA (3.0) GI filler (69.8) | 30 minutes |
| Example 8 | PAA liquid (72.0) HEMA (20.0) EGMPA (8.0) | GDMA (47.8) UDMA (41.8)) TEGDMA (7.0) Na•BSA (3.4) | Overnight |
| Comparative Example 9 | CD9038 (97.1) EGMPA (2.9) | N-phenyl glycine (NPG) | Not cured |
| Comparative Example 10 | HEMA (95.1) EGMPA (4.9) | Li•p-TSA | Not cured |
| Comparative Example 11 | HEMA (95.1) EGMPA (4.9) | Na•BSA | Not Cured |

Example 1

A Catalyst Part containing an acid-containing resin 4-META was mixed with a Base Part, which Catalyst Part and Base Part contained the components and amounts thereof shown in Table 2 for Example 1. A living polymer formed when mixing the two parts. The Catalyst Part, however, also contains photointiators so that the mixture is can be light curable when radiated by external light source. The Catalyst Part and the Base Part were mixed in a 1:1 ratio by volume and reaction occurred at room temperature. After mixing the two parts, the mixture was placed between two glass slides sitting in the dark. The composition hardened in about 10 minutes and presented no visually seen residue monomer on its surface after separating the top slide. If the mixture is left in the mixing well but the top is open to air, however, the bottom part hardens, but there is a thick uncured layer present at the top even after 24 hours. Covering the uncured surface thereafter with a glass slide (directly contacting the material), the oxygen inhibited resin layer continues the cure and forms a hard and dried surface again in about 20 minutes.

Example 2

A Catalyst Part containing an acid-containing polymer PAA was mixed with a Base Part, which Catalyst Part and Base Part contained the components and amounts thereof shown in Table 2 for Example 2. The salt of the organic compound NTG-GMA.Na in the Base Part was completely dissolvable in the HEMA. The parts were mixed in a 1:1 ratio and the resulting composition was cured, between two glass slides, to a rubbery and flexible copolymer in about 10 minutes.

Example 3

A Catalyst Part containing an acid-containing polymer PAA was mixed with a Base Part, which Catalyst Part and Base Part contained the components and amounts thereof shown in Table 2 for Example 3. Upon mixing the parts in a 1:1 ratio, the viscosity of the mix increased greatly, in less than 2 minutes, and formed a sticky gel with a dried surface; which then cured to a hard solid in about 15 minutes. This example demonstrated a "living" resin modified glass ionomer composition (RMGI).

Example 4

A Catalyst Part containing an acid-containing polymer PAA in powder form was mixed with a Base Part, which Catalyst Part and Base Part contained the components and amounts thereof shown in Table 2 for Example 4. Upon mixing the powder and liquid, the acrylic acid appeared not to dissolve into the resin mix and maintained the solid form. Yet, the mix still hardened in about 20 minutes in the mixing well, leaving the bottom part more rigid (which showed more white powder within) and the top portion having a more soft feel.

Example 5

A Catalyst Part containing an acid-containing resin 4-META was mixed with a Base Part, which Catalyst Part and Base Part contained the components and amounts thereof shown in Table 2 for Example 5. A 1:1 mix of the two parts, when placed between two glass slides, cured into a hard composite in about 10 minutes.

Example 6

A Catalyst Part containing an acid-containing resin 4-META was mixed with a Base Part, which Catalyst Part and Base Part contained the components and amounts thereof shown in Table 2 for Example 6. Mixing a small amount of the NTG-GMA.Na powder into the polymerizable composite composition (about 0.3% by weight) and placing the mix between two glass slides sitting in dark, the composition cured completely into a hard and rigid composite sheet with a dry surface.

Example 7

A Catalyst Part containing an acid-containing PAA liquid was mixed with a Base Part, which Catalyst Part and Base Part contained the components and amounts thereof shown in Table 2 for Example 7. After 1:1 mixing of the two pastes by volume, the composition was used to fill a 3-mm diameter and 3-mm depth cylindrical cavity. The RMGI filling hardened in about 30 minutes and was surface dry.

Example 8

A Catalyst Part containing an acid-containing PPA liquid was mixed with a Base Part, which Catalyst Part and Base Part contained the components and amounts thereof shown in Table 2 for Example 8. The parts were mixed in a 1:1 ratio by volume in a dental mixing well. The viscosity increase was noticeable at 20 minutes. A viscosity increase was apparent in the bottom portion at a 50-minutes check. Placing some "uncured" top liquideous mixture between two glass slides and leaving it on a bench, the resin cured between two glass slides by the next day and was surface dry when removing the top glass cover.

Comparative Example 9

For comparison, a Catalyst Part containing EPMPA acid monomer was mixed with a Base Part, which Catalyst Part and Base Part contained the components and amounts thereof shown in Table 2 for Comparative Example 9. About 0.013 grams of NPG was mixed into 0.4 grams of the Resin Part (about 3.1% by weight of the NPG initiator concentration) and the composition was placed between two sets of glass slides. One set was placed on a bench at room temperature; the other set was placed in an oven at 54° C. In the following several hours, no apparent viscosity change was observed for the resin systems. After overnight sitting, however, some viscosity increase could be detected, with a viscosity increase in the set from the oven being more apparent. Thus, it appeared that the N-phenyl glycine compound alone is not as effective as its salt form.

Comparative Example 10

For comparison, a Catalyst Part containing EPMPA acid monomer was mixed with a Base Part, which non-Catalyst Part and Base Part contained the components and amounts thereof shown in Table 2 for Comparative Example 10. About 0.02 grams of the lithium salt of the organic compound Li.p-TSA was mixed into 1 gram of the Catalyst Resin part (which Base Part had about 0.2% by weight of the Li.p-TSA). Nothing appeared to happen after mixing the two parts, and the mixture remained a liquid even after several days.

Comparative Example 11

For comparison, a Catalyst Part containing EPMPA acid monomer was mixed with a Base Part, which Catalyst Part and Base Part contained the components and amounts thereof shown in Table 2 for Comparative Example 11. About 0.02 grams of the sodium salt Na.BSA was mixed into 1 gram of the Catalyst Part (which Base Part had about 0.2% by weight of the Na.BSA). Nothing appeared to happen after mixing the two parts, and the mixture remained a liquid even after several days.

Discussion: While Examples 1-10 have demonstrated that the organic compound that is at least partially water soluble and that, in the presence of an acid (that can be ionized or solvated to release radical ion groups) can be used in bulk polymerization as a part of the initiator system, the system required a certain concentration level of the salt in order to obtain effectiveness for starting the polymerization within a relatively short period of time.

Comparative Example 9 showed that when using a plain N-phenyl Glycine compound as part of the initiation system other than the disclosed derivative compounds the polymerization reaction was much slower or weak for the same or similar experimental conditions, which is not desirable from a practical view point. Based on Comparative Examples 10 and 11, it appears that when the salt of an organosulfur compound in the polymerizable composition is at a level of about 0.2% by weight or less, the organosulfur compound was not effective under the conditions tested for the initiation of the polymerization, or at least the polymerization did not occur within a reasonable time period. Therefore, it was desirable to have the initiator level in the polymerizable composition being about 0.2% by weight or greater in one side of the polymerizable system, specifically greater than 0.3% by weight, and most specifically greater than 0.5% by weight.

Examples 12-17

In the following Examples 12-17 the formation of living polymer showing "living" properties is illustrated. Taking some of the polymers/composites formed from previous examples, additional resin compositions were applied onto living polymer surfaces in order to observe the "living" property. These sequential additions of polymerizable resin compositions are in general inactive and will not produce polymerization reactions by themselves under normal storage conditions. If the composition is a light-curable formula, the composition will remain inactive as long as there is no light radiation exposure. The "living" nature of the living polymers/composites from the previous examples was surprisingly active with respect to additional resin layers not just once, but twice or even a multiples number of times in some cases. In order to more effectively obtain a cured surface (dry surface) of a living polymer, the polymerization reaction can be conducted under oxygen-free or anaerobic conditions.

TABLE 3

| Example No. | First Layer with Living polymers | Composition of Sequential Resin Layer | Polymerization time |
|---|---|---|---|
| Example 12A | The living polymers from Example 5 | First layer addition: CD9038 with 2.9% EGMPA | 15 minutes |
| Example 12B | Composite of Example 12A | Second layer addition: (The catalyst side of the Example 2) 4-META (10.3) UDMA (13.7) HEMA (5.1) TEGDMA (5.1) CQ (0.1) EDMAB (0.2) BHT (0.01) Silane treated Barium Glass filler (65.4) | 2 hours |
| Example 12C | Composite of Example 12B | Third layer addition: HEMA (19) NTG-GMA Na Salt (2) CN972 (12) GI Filler (67) | 30 minutes |
| Example 13 | The living polymer from Example 1 | First layer addition: 4-META (19.2) BisGMA (3.2) HEMA (9.6) BPO (2.7) BHT (0.2) Barium Glass filler (65.4) | 30 minutes |
| Example 14A | The living composite from Example 5 | First resin addition: The resin composition of the Catalyst Part used Example 5 | 10 minutes |
| Example 14B | The composite of Example 14A | Second resin addition: EGMPA resin as is | 15 minutes |
| Example 15A | The living composition of Example 6 | First layer resin addition: CD9038 with 2.9% EGMPA | Overnight check |
| Example 15B | Composite of Example 15A | Second resin addition: UDMA, TEGDMA and Bis(GDM)phosphate with CQ photo-initiator system | Overnight check |
| Example 16A | The living composition of Example 8 | First resin addition: CD9038 with 2.9% EGMPA | Overnight check |
| Example 16B | Composite of Example 16A | Second resin addition: Same CD9038 with 2.9% EGMPA resin mix | Next day check |
| Comparative Example 17A | Catalyst and Base of Example 2 of US U.S. Pat. No. 7,906,564 (to Jia et al.) | First resin addition: CD9038 containing 2.9% EGMPA | No reaction (Not curable) |
| Comparative Example 17B | Composite 17A | Second resin addition: EGMPA | No reaction (Not curable) |

Example 12A

In Example 12A, the polymeric material formed from previous Example 5 was used for applying a first and second layer of an additional resin compositions having the components and amounts thereof shown for Example 12 in Table 3. A drop of the first layer resin mix was placed onto the surface of the "living polymer" of Example 5 and then covered with a glass slide contacting the resin composition. In about 5 minutes, resistance could be felt when moving the top glass slide. In about 15 minutes, this additional layer cured completely. The cured surface was "dry" after removing the top glass slide.

Example 12B

The next day, another layer of resin was applied onto the cured surface of the composite of Example 12A and covered with a glass slide. The assembly was placed in dark to prevent light curing. The composite composition was again polymerized after about two hours.

Example 12C

After three days sitting on a bench, addition of a third resin layer addition was applied onto the previously cured second layer surface of the composite of Example 12B and covered with a glass slide. After about 30 minutes, the composition was hardened again, although it appeared that it was lacking adherence to the second layer of the composite.

Example 13A

In Example 13A, the polymeric material formed from previous Example 1 was used for applying a layer of additional resin composition having the components and amounts thereof shown for Example 13A in Table 3. A drop of resin composition was placed onto the surface of the "living polymer" of Example 1 and then covered with a glass slide contacting the resin composition. The composite was polymerized in about 30 minutes, even though the additional resin composition also contained BPO, a free radial polymerization initiator.

Example 14A

In Example 14A, the polymeric material formed from previous Example 6 was used for applying a layer of additional resin composition having the components and amounts thereof shown for Example 14A in Table 3. A drop of the resin composition without NTG-GMA.Na was placed on top of the cured composite surface, covered with a glass slide and placed in the dark. In about 10 minutes, the additional resin layer was cured, leaving the cured composite layer intact on the living composite surface after removing the covering glass;

Example 14B

In Example 14B, the polymeric composite formed from previous Example 14A was used for applying a second layer of additional resin composition having the components and amounts thereof that is shown for Example 14B in Table 3. A small drop of EGMPA resin was placed directly on the cured living composite surface of the previous layer, was covered again with a glass slide, and was allowed to cure. In about 15 minutes, the EGMPA resin hardened and it remain intact on the first additional layer of the living composite when removing the glass slide.

Example 15A

In Example 15A, the polymeric material formed from previous Example 7 was used for applying an additional layer of resin composition having the components and amounts thereof shown for Example 15A in Table 3. On the previously cured RMGI cylindrical filling top, a drop of the resin mix was added and covered with a glass slide. The additional resin layer was found cured in an overnight check.

Example 15B

In Example 15B, the polymeric composite formed from previous Example 15A was used for applying a second layer of additional resin composition having the components and amounts thereof that is shown for Example 15B in Table 3. After removing the cover glass from the cured resin layer surface of the composite of Example 15A, a second resin layer was added onto the cured resin surface again, covered with a glass slide, and placed in the dark. The resin was found cured after sitting overnight.

Example 16A

In Example 16A, the polymeric material formed from previous Example 8 was used for applying a layer of additional resin composition having the components and amounts thereof shown for Example 16A in Table 3. After removing the top cover glass from the cured resin film surface, a drop of the first layer resin was added and covered by the glass again. In an overnight check, the resin addition was found cured, leaving a "wet"-free surface when removing the top glass cover.

Example 16B

In Example 16B, the polymeric composite formed from previous Example 16A was used for applying a second layer of additional resin composition having the components and amounts thereof that is shown for Example 16B in Table 3. Another layer of resin was added onto the previously cured solid surface and covered with the glass cover. The resin had once again found cured on checking the next day.

Comparative Example 17A

In Comparative Example 17A, a self-cured dental composite material of conventional free radical polymerization (through the redox reaction of BPO and DHEPT) by mixing of the Catalyst Part and Base Part of Example 2 of U.S. Pat. No. 7,906,564 (to Jia et al.). After adding a drop of the polymerizable resin onto the self-cured composite surface and covering with a glass slide, the resin underneath was found to be still liquid, and the glass slide was freely removable even after two days, indicating that the resin addition did not go through polymerization;

Comparative Example 17B

In Comparative Example 17B, a second layer of additional resin composition having the components and amounts thereof that is shown for Example 16B in Table 3 was added to the composite of Example 17A. As in Comparative Example 17A, again no reaction was observed.

Discussion: Based on Examples 12-17, the "living" nature of the living polymers/composites, using resin systems of previous examples, was found to be surprisingly active for not just one additional resin layer, but twice or even multiples layers in some cases.

Examples 18-23

Testing: A pocket sized "Geotester" penetrometer (available from an online company "CertifiedMaterialTestingProducts.com") was used for measuring the cohesiveness of the resin material during the process of the living polymerization. This device was initially designed for use with soil. It can give an estimated unconfined compressive strength directly in $kg/cm^2$ when used with the standard ¼ inch diameter plunger. When in testing, the plunger is pressed into the curing composition to the calibration notch (which is about 6 mm from the plunger end). The maximum value is retained on the dial until released by a push button. The inner dial scale is 0-6.0×0.1 divisions in $kg/cm^2$. The outer scale gives shear strength over 0-11 kg range×0.1 kg divisions, and this reading is used with charts provided to estimate bearing pressures depending on plunger used and soil type. Three reading were taken at each reading time and report the average number in the table below.

The testing samples were prepared by mixing enough 1:1 by volume of the Catalyst and Base parts of the polymerizable composition as the table below indicated on a mixing paper or a mixing container using a dental spatula first.

While the mixture is still in fluid and soft state (after about 30 seconds mixing time), transfer the mixture into a cylindrical plastic mold having an inner diameter of one inch and height of 0.75 inches and level the material with the top of the mold and cover it with a glass slab to form an oxygen barrier to the curing material. When in testing, the cover glass is removed and the testing material is exposed. Then, the plunger of the penetrometer tester was applied by pushing down to the polymerizing material surface to the calibrated mark on the plunger at certain intervals to give a reading in $kg/cm^2$ to show the cohesiveness nature at that time period of the polymerization. When removing the penetrometer tester plunger from the test materials' surface, the poked dents are repacked or smoothed out with a dental spatula to achieve a leveled surface again until the next test period.

Based on the experimental observation, when the test material is liquideous or soft, which may mean it has not polymerized or in the early stage of polymerization, the penetrometer reading is usually low or zero depending on the test material composition. The cohesiveness of the polymerizing compound increases with the degree of the polymerization. Therefore, a higher penetrometer reading could be obtained when the polymerization started. Once the polymerization reaches a maturing state, the Geo penetrometer tester would not be able to give meaningful reading, as the plunger of the tester will not be able to penetration into the polymerized mass. From a practical aspect, it was observed that when the penetrometer gives a reading of 2.0 $kg/cm^2$ or more, the penetration of the tester plunger into the curing composition to the calibrated mark on the plunger is very difficult and the hand pushing action has reached a point of being very stressful. The plunger then may not be able to reach the calibration mark and may only show an incomplete circular dent on the material surface. That is usually an indication of the polymerizing material being at the maturing point or approaching to the maturing point of the polymerization process. For the reading number of about 0.8-1.5 $kg/cm^2$, the material has the proper resistance to packing and condensing action with the least stickiness and messiness of the material. Of course, deviations in the reading values of using the penetrometer may be present for different composition make-ups. Therefore, the suggested values presented here should not be deemed as a "standard". Nevertheless, with a conventional redox reaction induced polymerization, such as a benzoyl peroxide/amine system, because of the curing rate usually being fast and the cohesiveness of the polymerizing resins increased abruptly, the stage when the curing mass is in a "manipulatable" state is usually very short and is less than 30 seconds.

The compressive strength test samples were 4 mm diameter and 6 mm in height. Samples were prepared by mixing 1:1 (volume) of the corresponding Catalyst and Base using a dental plastic spatula for 30 seconds before filling the mixture into the cylindrical TEFLON mold. Five samples for each test group were prepared. For Compressive Strength 1 samples, the materials were filled into the molds right away without further manipulation. For Compressive Strength 2 samples, after the materials mixing, it is waited until the material reaches the "intermediate stage of living polymerization" and then is filled into the molds using packing and condensing actions. The top and bottom of the mold were then covered by two glass slides and tightened with a small size "C" clamp after the filling done for one hour before placing the samples within the mold but with the clamp removed into water and placing in 37° C. oven for 24 hours before the crushing test. At 24 hours, the samples were separated from the mold and then compression tested by using a universal testing machine, Admet eXert® 5603 (Admet Inc., MA), with a cross-head speed of 0.75 mm/minute. The results of the average with standard deviation were calculated and reported by the machine for each test group as listed in the table below.

As can be seen by the results below, the packing and condensing actions during the "intermediate stage of living polymerization" appears will not interfere with the mechanical properties of the materials tested. Rather, it can actually help to improve the properties. In particular, the increase of the compressive strengths for the condensed test samples vs. the regular prepared samples indicates that the condensing action during the "intermediate stage of living polymerization" makes the test sample denser or less voids within. Therefore, less defects are formed in the samples.

Examples 18-20

The following Examples 18-20 demonstrated the presence of the extended "working" periods (the "intermediate stage of living polymerization") for the present two-part self-curable compositions after the living polymerization had started. Table 4 below lists the compositional formula for each Catalyst and Base Part of the cure system. All the ingredient contents are in parts per hundred (percentages by weight) in the formulas unless otherwise stated.

TABLE 4

| Components | Example 18 Catalyst | Example 18 Base | Example 19 Catalyst | Example 19 Base | Example 20 Catalyst | Example 20 Base |
|---|---|---|---|---|---|---|
| PAA liquid | 24.7 | | | | | |
| HEMA | 13.3 | | 7.8 | | 2.5 | |
| GDMA | | 17.5 | 3.7 | 11.3 | 5.0 | 8.6 |
| UDMA | | 14.8 | 3.3 | 9.8 | 3.5 | 7.3 |
| TEGDMA | | 2.7 | 0.6 | 1.7 | 1.0 | 1.2 |
| HEMA-Phosphate | | | 2.6 | | 3.7 | |
| 4-META | | | 17.6 | | 17.2 | |
| Water | | | | | 3.0 | |
| Epoxy 06 | | | | | | 17.4 |
| EDMAB | | | | | | 0.3 |
| CQ | | | | | | 0.1 |
| Barium Glass Filler | 62 | | 61.6 | | 61.6 | 60.2 |
| Gl filler | | | | 72.3 | | |
| $Ca_3(PO_4)_2$ | | 64.0 | | | | |
| Zinc Oxide | | | | 2.0 | | |

TABLE 4-continued

| Components | Example 18 Catalyst | Example 18 Base | Example 19 Catalyst | Example 19 Base | Example 20 Catalyst | Example 20 Base |
|---|---|---|---|---|---|---|
| Amorphous silica | | | 2.9 | 2.1 | 2.5 | 2.4 |
| NTG-GMA. Mg Na. BSA | | | | 0.8 | | 2.5 |
| Li. p-TSA | | 1.0 | | | | |
| Yellow iron oxide pigment Yellow 8087 | | | | ≤0.02 | | |
| Consistency of the formed Pastes | Dough/putty consistency | Dough/putty consistency | Soft and creamy paste | Soft and creamy paste | Flowable paste | Flowable paste |
| Cohesiveness Readings | 0.6 kg/cm² | 0.45 kg/cm² | 0 | 0 | 0 | 0 |

Example 18

In Example 18 of Table 4, the Catalyst and Base was mixed for 60 seconds in a ratio of 1:1 by volume, before transferring the mix to a test mold. As evident by the results in Table 5 below, after 23 hours overnight the penetrometer reading was 2.0 kg/cm² and the surface of the mold was not penetrable by the plunger to the mark, which only left a dent from pressing the plunger. Based on these results, it can be concluded that the formulation of Example 18 exhibited a long "intermediate stage of living polymerization" that was at least about two hours long.

Furthermore, polymerization of an additional resin layer on the cured surface, 24 hours after the penetrometer test was completed, obtained a cured composite, wherein the additional resin layer consisted of CD9038 containing 2.9% EGMPA, wherein the hardened composite was cured anaerobically. The product showed satisfactory compressive strength, as shown by the results in Table 5.

Example 19

In Example 19 of Table 4, the Catalyst and Base was mixed for 30 seconds in a ratio of 1:1 by volume, before transferring the mix to a test mold. As evident by the results in Table 5 below, after 6.0 to 6.5 minutes the mixture obtained a penetrometer reading of >2.0 kg/cm², and the surface was no longer penetrable to the calibration mark, only leaving a dent from plunger pressing. Thus, this example 19 showed a relatively short presence of the "intermediate stage of living polymerization" that was about one minute.

Polymerization of an additional resin layer on the cured surface, 24 hours after the penetrometer test was completed, obtained a cured composite, wherein the additional resin layer consisted of CD9038 containing 2.9% EGMPA, producing a hardened composite that cured anaerobically. Furthermore, the product showed excellent compressive strength, as shown by the results in Table 5.

Example 20

In Example 20 of Table 4, six grams of each of the Catalyst and Base was mixed together for 30 seconds before transferring the mix to a test mold. As evident by the results in Table 5 below, after one hour 15 minutes from the start the surface was no longer penetrable to the calibration mark. Thus, the epoxy-containing composition of Example 20 showed the presence of an "intermediate stage of living polymerization" that was about twenty minutes.

In further testing, polymerization of an additional resin layer on the cured surface, 24 hours after the penetrometer test was completed, obtained an anaerobically cured/hardened composite, wherein the additional resin layer consisted of CD9038 having 2.9% EGMPA. The product showed excellent compressive strength, as shown by the results in Table 5.

TABLE 5

| Testing time intervals | Catalyst and Base of Example 18 Penetrometer readings (by range, kg/cm²) | Catalyst and Base of Example 19 Penetrometer readings (by range, kg/cm²) | Catalyst and Base of Example 20 Penetrometer readings (by range, kg/cm²) |
|---|---|---|---|
| Initial Readings (each paste "as is") | 0.45-0.60 | 0-0 | 0-0 |
| 3.5-4.5 minutes | 0.75 | 0.3-0.8 | 0 |
| 4.5-5.5 minutes | 0.75 | 0.8-1.2 | 0 |
| 6.0-6.5 minutes | 0.75 | >2.0 | 0 |
| 6.5-18 minutes | 0.75 | — | 0 |
| 30-45 minutes | 0.9-1.0 | — | 0.1-0.4 |
| 50-60 minutes | — | — | 0.5-1.5 |
| 1 hours-2.5 hours | 1.0-1.3 | — | 1.5-2.0 |
| @23 hours/overnight | >2.0 | — | — |
| Self-cured Compressive Strength 1* (MPa) | 9.3 (1.1) | 145.2 (6.9) | 134.1 (5.2) |

TABLE 5-continued

| Testing time intervals | Catalyst and Base of Example 18 Penetrometer readings (by range, kg/cm$^2$) | Catalyst and Base of Example 19 Penetrometer readings (by range, kg/cm$^2$) | Catalyst and Base of Example 20 Penetrometer readings (by range, kg/cm$^2$) |
|---|---|---|---|
| Self-cured Compressive Strength 2** (MPa) | 9.5 (1.3) | 159.7 (8.5) | 138.6 (4.6) |

*This compressive strength value was obtained from the test samples without utilizing the "intermediate stage of living polymerization," i.e., both sides of the test materials were mixed and loaded into the mold while it was just mixed and the immediately clamped to allow self-cure without any condensing actions being applied to the materials during the sample preparation, except for Example 20, which has a putty consistence to begin with;
**This is the compressive strength value from samples that utilized packing and condensing actions during the "intermediate stage of living polymerization" to fill the material into the mold, following by clamping to allow further self-cure.

Examples 21-23

Each of the additional Examples 21-23 in Table 6 below further demonstrated the presence of an extended "working period" (an "intermediate stage of living polymerization") after living polymerization had started.

TABLE 6

| Components | Example 21 Catalyst | Example 21 Base | Example 22 Catalyst | Example 22 Base | Example 23 Catalyst | Example 23 Base |
|---|---|---|---|---|---|---|
| PAA liquid (about 50% solids) | 26.5 | | 8.0 | | 23.3 | |
| HEMA | 6.6 | | 2.0 | | 5.8 | |
| GDMA | | 11.5 | 10.0 | 11.5 | | 12.5 |
| UDMA | | 9.75 | | 9.75 | | 10.6 |
| TEGDMA | | 1.75 | | 1.75 | | 1.9 |
| HEMA-Phosphate | | | 20.0 | | 12.9 | |
| EDMAB | | | | | | 0.55 |
| CQ | | | | | | 0.04 |
| Barium Glass Filler | 66.9 | | 60.0 | | 57.95 | 70.08 |
| Gl filler | | 74 | | 74 | | |
| Ca$_3$(PO$_4$)$_2$ | | | | | | 1.8 |
| Zinc Oxide | | 1.0 | | 1.0 | | 1.4 |
| Amorphous silica | | 1.5 | | 1.5 | | 0.5 |
| NTG-GMA. Mg Na. p-TSA | | 0.5 | | 0.5 | | 0.62 |
| BHT | | | | | 0.02 | 0.01 |
| Yellow iron oxide pigment, Yellow 8087 | | | | | <0.03 | |
| Consistency of the formed Pastes | Soft and creamy paste | Soft and creamy paste | Flowable paste | Flowable paste | Flowable paste | Flowable paste |
| Cohesiveness Readings | 0 | 0 | 0 | 0 | 0 | 0 |

As described above, a Geotester® penetrometer was used for measuring the cohesiveness of the resin material during the process of the living polymerization for the compositions described above for Examples 18-20. The Geotester® readings during the polymerization process, at various time frames, as well as the compressive strength with or without condensing/packing actions during the polymerization process are shown in Table 7 below.

TABLE 7

| Testing time intervals | The Catalyst and Base of Example 21 Penetrometer readings (by range, kg/cm$^2$) | The Catalyst and Base of Example 22 Penetrometer readings (by range, kg/cm$^2$) | The Catalyst and Base of Example 23 Penetrometer readings (by range, kg/cm$^2$) |
|---|---|---|---|
| Initial Readings (each paste as is) | 0-0 | 0-0 | 0-0 |
| 30 seconds-1.5 minutes | 0.1-0.2 | 0 | 0 |
| 2-3 minutes | 0.3-0.4 | 0.5-0.6 | 0.2-0.8 |
| 3.0-4.0 minutes | 0.3-0.5 | 1.2-2.2 | 1.2-1.6 |
| 4-5 minutes | 0.4-0.5 | >2.5 | 1.7-2.5 |

TABLE 7-continued

| Testing time intervals | The Catalyst and Base of Example 21 Penetrometer readings (by range, kg/cm$^2$) | The Catalyst and Base of Example 22 Penetrometer readings (by range, kg/cm$^2$) | The Catalyst and Base of Example 23 Penetrometer readings (by range, kg/cm$^2$) |
|---|---|---|---|
| 5-6 minutes | 0.4-0.5 | Surface hard | Surface hard |
| 9-16 minutes | 0.7-1.1 | — | — |
| 17-20 minutes | 1.9-2.3 | — | — |
| 30 minutes | Set and hard | — | — |
| Length of the "intermediate stage of living polymerization" | About 5 minutes | About 1 minute. | About 1.5 minutes |
| Polymerization of an additional resin layer? | Yes | Yes | Yes |
| Self-cured Compressive Strength 1 (MPa) | 133.4 (4.5) | 164.2 (4.6) | 154.3 (14.6) |
| Self-cured Compressive Strength 2 (MPa) | 145.0 (5.2) | 170.5 (10.8) | 172.1 (9.8) |

Example 21

The Catalyst and Base Parts of Example 21 in Table 6 was mixed in a ratio of 1:1 by volume for 30 seconds before transferring the mix to a test mold. As evident by the results in Table 7, after 3.0-4.0 minutes the paste had turned into a putty consistency. After 17-20 minutes a reading of 1.9-2.3 kg/cm$^2$ indicated that the surface was no longer penetrable to the mark, only leaving a shallow dent at the later stage. After 30 minutes, the material had set, and the surface was no longer penetrable. Thus, this Example 21 demonstrated a system that had an "intermediate stage of living polymerization" of about 5 minutes.

Furthermore, polymerization of an additional resin layer onto the cured surface, one hour after the penetrometer test was completed, obtained a cured composite. The additional resin layer was the resin CD9038 containing 2.9% EGMPA, which was applied on top of the cured/hardened mixture. The composite cured anaerobically within one hour.

The product showed excellent compressive strength, as shown by the results in Table 7.

Example 22

The Catalyst and Base Parts of Example 22 in Table 6, in an amount of 5 grams of each Part, were mixed together for 30 seconds before transferring the mix to a test mold. As evident by the results in Table 7, nearing 4 minutes the surface was still penetrable to the calibration mark, although the cohesiveness reading was higher. After 4 to 5 minutes, however, the surface was no longer penetrable to the mark, only leaving a shallow dent. After 5 to 6 minutes, the surface was hard. Accordingly, Example 21 demonstrated a system that had an "intermediate stage of living polymerization" of about 5 minutes, a relatively short presence of an "intermediate stage of living polymerization."

In further testing, polymerization of an additional resin layer onto the cured surface, one hour after the penetrometer test was completed, obtained a cured composite. The additional resin layer contained resin CD9038 having 2.9% EGMPA, which was applied on top of the cured/hardened mixture. The composite cured anaerobically in less than 30 minutes.

The product showed excellent compressive strength, as shown by the results in Table 7.

Example 23

The Catalyst and Base Parts of Example 23 in Table 6, in an amount of 5 grams of each Part, were mixed together for 30 seconds before transferring the mix to a test mold. As evident by the results in Table 7, after 3 to 4 minutes the surface was penetrable to the calibration mark. After 4 to 5 minutes, however, the surface was no longer penetrable to the mark, only leaving a shallow dent or no dent at the later stage. After 5 to 6 minutes, the surface was hard and no longer dent forming. Thus, this Example 23 demonstrated a system that had an "intermediate stage of living polymerization" of only about 1.5 minutes.

Furthermore, polymerization of an additional resin layer onto the cured surface, one hour after the penetrometer test was completed, obtained a cured composite. The additional resin layer was the resin CD9038 containing 2.9% EGMPA, which was applied on top of the cured/hardened mixture. The composite cured anaerobically in less than 30 minutes.

The product showed excellent compressive strength, as shown by the results in Table 7.

Comparative Example 24

A self-cured dental composite material of conventional free radical polymerization (through the redox reaction of BPO and DHEPT, as well as a salt of sulfinic acid) was obtained by mixing the Catalyst and Base of Example 2 of U.S. Pat. No. 7,906,564 (to Jia et al.). The cohesiveness of the mixture was measured, using the Geotester® instrument and technique for testing as described above. The results are shown in Table 8 below.

TABLE 8

| Time of the cohesiveness measurement | Geotester ® Reading (kg/cm$^2$) |
|---|---|
| Initial | 0 |
| 0.5-2 minutes | 0 |
| 2.5-3 minutes | 0 |
| 3.5 minutes | 0 |
| 4 minutes | Greater than 2 |

After 2.5 to 3 minutes, the mixture showed a viscosity increase and gelled, indicating entering into "gel time," and was sticky. After 3.5 minutes, the test plunger penetrated easily through the matrix to reach the mark; and the indent formed was permanent without registering a cohesiveness force. The material surface was then not able to be smoothed level after removing the plunger. After 4 minutes, the material was hard like a rock, and no indent could be made.

This comparative example formula utilized a salt of sulfinic acid as one of the co-redox curing initiators, which promoted a sharp cure for the self-curing reaction. Apparently, due to the co-existence of an excessive amount of benzoyl peroxide among other ingredients, there was an absence or lack of an "intermediate stage of living polymerization," even though the comparative example composition contained an acid-containing 4-META resin, a polymerizable monomer, and a salt of sulfinic acid. Apparently, the additional active components co-present in the composition prevented obtaining living properties or terminated the living polymerization.

Discussion: The significance of having the "intermediate stage of living polymerization," during which period there is an internal cohesive stress of about 0.5 to about 2.0 kg/cm$^2$ for the living polymerizable compositions, is that during an in situ application of the compositions one can turn an initially a soft, sticky and flowable material having low or zero internal cohesiveness (as measured by using a penetrometer) into a material having putty-like viscosity that has increased internal cohesiveness that becomes non-sticky, moldable, pressable and/or condensable. This result can facilitate application of the material and renders the material user friendly, which allows the material to be packaged and auto-mixed, for example, using Mix-Pac™ dual barrel cartridges, as it is well known in dentistry for packaging and delivery of dental resin cements.

Accordingly, a dentist or other operator can inject the present material formed from a kit directly into a tooth cavity and allow it to firm up within the cavity to reach the "intermediate stage of living polymerization." The operator can then use a proper dental instrument commonly used for high filled resin composites and/or for dental amalgam alloy materials to pack, shape, adapt or condense the restorative material, well into the cavity, for at least 30 seconds before it reaches the set state. Furthermore, one could also conduct the packing/condensing action in conjunction with the restoration surface finishing procedure, all together, as in the case of a dental amalgam filling process, without using any subsequent dental burs or finishing instruments commonly driven by a dental electric or turbine hand piece. Such practice would be especially suitable for places where electricity is lacking or where standard dental practice is not feasible, for example, where practice of ART (Atraumatic Restorative Treatment) is necessary.

The invention claimed is:

1. A method of forming a cured solid material from polymerizable resin system comprising:

mixing a first Part A and a second Part B, at least one of which is a paste, that, within 6 hours after beginning mixing, obtains a working period of intermediate stage polymerization providing a manipulative state of cohesiveness characterized by a stress unit measurement of 0.5 to 2.0 kg/cm$^2$, as measured with a penetrometer, which working period lasts for 45 seconds to 24 hours, that allows a predetermined working period for applying the mixture; and applying the mixture as an adhesive, cement, glue, sealant, a base liner, a capping agent, a material for surface or structural repair and/or filling, an encasing material, a bodily implant, a dental material, and/or as a polymeric object having a living polymer surface property before the mixture becomes a cured solid material, wherein the first Part A comprises an acid, wherein the acid comprises polyacrylic acid homopolymer or copolymer, 4-methacryloxyethyl trimellitic anhydride or 4-methacryloxyethyl trimellitic acid;

wherein the second Part B comprises an organic compound that is water soluble or partially water soluble and that, in the presence of the acid can be ionized or solvated to initiate curing of one or more ethylenically unsaturated monomers or oligomers that is present in Part A, Part B, or both, wherein the organic compound is a salt of organic acid, an onium compound, protonated amines, and precursors thereof, as well as combinations thereof ; and wherein the one or more ethylenically unsaturated monomers and/or oligomers are chosen from the group consisting of acrylonitrile, acrylamide, (meth)acrylates, aldehydes, butadiene-1,3, ethylene, isoprene, methacrylic esters, methacrylamide, methyl styrene, styrene, vinyl esters, vinylidene chloride, and N-vinyl pyrrolidone, and combinations thereof.

2. The method of claim 1, wherein the first Part A and the second Part B that, within 6 hours after mixing to form a paste, provides a working period of intermediate stage polymerization in which the paste obtains a cohesiveness characterized by a stress unit measurement of 0.8 to 1.9 kg/cm$^2$, as measured with a penetrometer, which working period lasts for 1 minute to 2 hours.

3. The method of claim 1, wherein the second Part B comprises at least 0.2 wt. % of a salt of phenylglycine and derivatives thereof represented by the following structure (1) or organosulfur compounds represented by the following structure (2):

$$R^1C_6H_4NR^2CH_2COO^-M^+, \quad (1)$$

wherein $R^1$ is hydrogen or a substituted or unsubstituted alkyl group; $C_6H_4$ is a phenyl group; $R^2$ is a hydrogen or a substituted or unsubstituted alkyl group optionally comprising a functional group that is vinyl, acrylate, or methacrylate; M+ is a metal cation to compensate electric charges; and

$$R-S(O)_n-O^-X^+ \quad (2)$$

wherein R is an organic radical; n =0, 1 or 2; and $X^+$ is a metal cation to compensate electric charges, or combinations of compounds of structures (1) and (2).

4. The method of claim 3, wherein the R group in structure (2) is a substituted or unsubstituted $C_1$-$C_{10}$ alkyl or $C_6$-$C_{12}$ aryl, wherein substituents are optionally selected from the group consisting of halogen, oxy, alkoxy, hydroxy, amino and/or imino radicals.

5. The method of claim 1, wherein the first Part A, the second Part B, or both, further comprises an inorganic filler in an amount of up to about ninety-five percent by weight of each component.

6. The method of claim 1, wherein the acid in first Part A comprises poly(acrylic acid) homopolymer or a copolymer.

7. The method of claim 1, wherein the acid in first Part A comprises 4-methacryloxyethyl trimellitic anhydride or 4-methacryloxyethyl trimellitic acid.

8. The method of claim 1, wherein the acid comprises poly(acrylic acid) in combination with an acid monomer containing a phosphoric acid group.

9. The method of claim 8, wherein the acid monomer is methacrylate monomer having a phosphoric acid group.

10. The method of claim 1, wherein the one or more ethylenically unsaturated monomers and/or oligomers is an acrylate or a methacrylate.

11. The method of claim 1, wherein the first Part A, the second Part B, or both, further comprises photoinitiators and/or redox initiators, polymerization inhibitors, stabilizers, UV absorbers, radiopaque materials, fluorescent agents and therapeutic agents.

12. The method of claim 1 wherein the polymerizable resin system formed from admixture of Part A and Part B is a dental composition that is used as cement or restorative filling material, a bonding agent, a restorative composite, a root canal sealant, base liner, or a pulp capping agent.

13. The method of claim 12 further employing the polymerizable resin system to fill a space by packing and condensing actions during the working period of intermediate stage polymerization.

14. The method of claim 1 wherein the mixed composition is injected into a tooth cavity as a restorative material, allowed to firm up to reach an intermediate stage of living polymerization, and a dental instrument is used to pack, shape, adapt or condense the restorative material into the cavity for at least 30 seconds before it reaches the set state.

15. The method of claim 1 wherein the polymerizable resin system is used to form a pre-made polymeric article having a living-polymer surface that is delivered to another location for use in filling a space or for placement in a predetermined site and wherein the pre-made polymeric article is glued into a predetermined site using an ethylenically unsaturated polymerizable adhesive composition that is polymerizable by contact with a polymer surface of the article in order to secure the pre-made polymeric article in the predetermined site.

16. The method of claim 15 wherein the pre-made polymeric article is a dental crown or bridge, an inlay/onlay, a root canal point, or post to restore a damaged tooth.

* * * * *